(12) United States Patent
Song et al.

(10) Patent No.: US 11,311,652 B2
(45) Date of Patent: Apr. 26, 2022

(54) ZWITTERIONIC HYDROGELS FOR DELIVERY OF BIOMOLECULES

(71) Applicant: University of Massachusetts, Boston, MA (US)

(72) Inventors: Jie Song, Shrewsbury, MA (US); Pingsheng Liu, Worcester, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 16/598,024

(22) Filed: Oct. 10, 2019

(65) Prior Publication Data

US 2020/0038558 A1    Feb. 6, 2020

Related U.S. Application Data

(63) Continuation of application No. 15/321,542, filed as application No. PCT/US2015/039227 on Jul. 6, 2015, now abandoned.

(60) Provisional application No. 62/022,187, filed on Jul. 8, 2014.

(51) Int. Cl.
| | |
|---|---|
| A61L 27/44 | (2006.01) |
| A61L 27/58 | (2006.01) |
| A61K 38/18 | (2006.01) |
| A61L 27/54 | (2006.01) |
| A61K 38/30 | (2006.01) |
| A61L 27/14 | (2006.01) |
| A61L 27/50 | (2006.01) |
| A61L 27/18 | (2006.01) |
| A61L 27/52 | (2006.01) |

(52) U.S. Cl.
CPC .............. *A61L 27/58* (2013.01); *A61K 38/18* (2013.01); *A61K 38/1875* (2013.01); *A61K 38/30* (2013.01); *A61L 27/14* (2013.01); *A61L 27/18* (2013.01); *A61L 27/50* (2013.01); *A61L 27/52* (2013.01); *A61L 27/54* (2013.01); *A61L 2300/414* (2013.01); *A61L 2430/02* (2013.01)

(58) Field of Classification Search
None
See application file for complete search history.

(56) References Cited

PUBLICATIONS

Martinovic et al., J. Histochem. Cytochem., 2004, 52(9), pp. 1159-1167. (Year: 2004).*
Liu et al., Biomaterials, 2013, 34(10), pp. 2442-2454 & its supplemental information. (Year: 2013).*

* cited by examiner

*Primary Examiner* — Brian Gulledge
(74) *Attorney, Agent, or Firm* — Milstein Zhang & Wu LLC

(57) ABSTRACT

The invention provides a novel approach in which zwitterionic networks are used to sequester and deliver ionic biomolecules, such as proteins, without compromising their native conformation and bioactivity. Zwitterionic networks are designed to effectively retain and deliver ionic or polar biomolecules for guided tissue regeneration. The invention represents a conceptual advance and enables a novel strategy for the utilization of zwitterionic motifs as therapeutics delivery vehicles and tissue engineering scaffolds.

10 Claims, 15 Drawing Sheets

ZWITTERIONIC HYDROGELS FOR DELIVERY OF BIOMOLECULES

PRIORITY CLAIMS AND RELATED PATENT APPLICATIONS

This application is the continuation of and claim the benefit of priority to U.S. Utility application Ser. No. 15/321,542, filed Dec. 22, 2016, which is the U.S. national phase of and claims priority to PCT/US15/39227, filed Jul. 6, 2015, which claims the benefit of priority to U.S. Provisional Application Ser. No. 62/022,187, filed Jul. 8, 2014, the entire content of each of which is incorporated herein by reference in its entirety.

GOVERNMENT RIGHTS

This invention was made with Government support under grant no. AR055615 awarded by the National Institutes of Health. The Government has certain rights in the invention.

TECHNICAL FIELD OF THE INVENTION

The invention generally relates to biomaterials, tissue engineering and delivery of biomolecules. More particularly, the invention relates to zwitterionic polymers and methods of their applications in delivery of biomolecules and tissue engineering.

BACKGROUND OF THE INVENTION

Zwitterions, including phosphobetaine, sulfobetaine, and carboxybetaine, are well-known for their anti-biofouling properties as widely demonstrated on 2-dimensional (2D) surfaces. The unique zwitterionic structures, simultaneously possessing cationic and anionic residues yet overall electronic neutral, exhibit strong affinity for water, thereby giving rise to super hydrophilic surfaces suppressing the hydrophobic interactions known to denature proteins. (Lowe, et al. 2002 *Chemical reviews* 102:4177-89; Seo, et al. 2008 *Biomaterials* 29:1367-76; Krishnan, et al. 2008 *J Mater Chem* 18:3405-13; Kane, et al. 2003 *Langmuir* 19:2388-91.)

Zwitterionic motifs have also been shown to mimic the action of protein stabilizing ions in stabilizing/maintaining the native conformation of proteins and inhibiting non-specific protein adsorption, which is known to set off undesired cascades of surface events (e.g., thrombosis, immune response). Accordingly, they have been largely exploited for constructing anti-fouling surfaces/interfaces to inhibit protein, bacterial and cellular adhesions, and as bioinert implants for reducing scar tissue formation. (Nakaya, et al. 1999 *Prog Polym Sci* 24:143-81; Zhang, et al. 2003 *Biomaterials* 24:4223-31; Jiang, et al. 2010 *Adv Mater* 22:920-32; Smith, et al. 2012 *Sci Transl Med* 4, 153; Ishihara, et al. 1998 *J Biomed Mater Res* 39:323-30; Yuan, et al. 2003 *Colloid Surface B* 29:247-56; Franz H. Zur Lehre von der Wirkung der Salze. Archiv für Experimentelle Pathologie and Pharmakologie 1888; 25; Han, et al. 2007 *Sci China Ser B* 50:660-4; Keefe, et al. 2012 *Nat Chem* 4:60-4; Zhang, et al. 2013 *Nat Biotechnol* 31:553-6; Harris J M. *Poly(ethyleneglycol) chemistry: biotechnical and biomedical applications*. New York: Plenum Press; 1992; Horbett, et al. 1995 *Proteins at Interfaces II: Fundamentals and Applications* Washington, D.C.: Am. Chem. Soc.)

Recently, the use of zwitterionic sublfobetaine hydrogel to facilitate templated biomineralization was reported, which capitalizes on the ability of the zwitterionic motifs to effectively recruit/nucleate oppositely charged mineralization precursor ions (e.g., $Ca^{2+}$, $PO_4^{3-}$) across the 3D hydrogel network. (Liu, et al. 2013 *Biomaterials* 34:2442-54.)

There is little report, however, on whether 3-dimensionally presented zwitterions can effectively sequester ionic biomolecules. Such a property, if intrinsically exists, could fundamentally change the current perception of zwitterionic materials as being primarily anti-biofouling and significantly broaden its potential use in biomedical applications. It is strongly desired that novel methods and compositions are uncovered and developed that greatly expand the utility of zwitterionic materials in the bioengineering and therapeutics areas.

SUMMARY OF THE INVENTION

The invention provides a novel approach in which zwitterionic materials are utilized to retain and deliver ionic biomolecules, such as proteins, for guided tissue regeneration. The invention uncovers and takes advantage of the ability of zwitterionic networks to sequester ionic biomacromolecules without compromising their native conformation and bioactivity, which challenges the conventional narrow perception and categorization of zwitterionic materials as low-fouling and bioinert. The invention demonstrates that zwitterionic networks are versatile vehicles useful in engineering controlled bioactive microenvironment for biomedical applications.

The invention represents a conceptual advance and enables a novel strategy for the utilization of zwitterionic motifs as therapeutics delivery vehicles and tissue engineering scaffolds. The invention distinguishes zwitterionic materials from the current benchmark biocompatible and anti-fouling material poly(ethylene glycol) (PEG) that is widely used in the biomaterials field. The ability of the zwitterionic hydrogel to promote the functional bone healing with an exceptionally low dose of therapeutic proteins, as demonstrated herein, can significantly reduce the cost as well as improve the safety associated with the protein therapeutics.

In one aspect, the invention generally relates to a composite material comprising a polymer network and a biologically active compound, wherein the 3-dimensional polymer network comprises a zwitterionic moiety.

In another aspect, the invention generally relates to an implant comprising a composite material characterized by a 3-dimensional crosslinked polymer network sequestered therein one or more biologically active compounds, wherein the polymer comprises a zwitterionic moiety.

In yet another aspect, the invention generally relates to an implant comprising a 3-dimensional scaffold comprising a 3-dimensional polymer network, wherein the polymer network comprises a zwitterionic moiety, adapted to sustained in vivo delivery of one or more biologically active compounds.

In yet another aspect, the invention generally relates to an implant comprising a n implant comprising a composite material characterized by a 3-dimensional crosslinked polymer network comprising a zwitterionic moiety.

In yet another aspect, the invention generally relates to a method for making a composite material useful for tissue engineering. The method includes crosslinking, in the presence of a biologically active compound, a polymer comprising a zwitterionic moiety to form a 3-dimensional crosslinked polymer network with the biologically active compound encapsulated therein.

In yet another aspect, the invention generally relates to a method for making a composite material useful for tissue engineering. The method includes: crosslinking a polymer comprising a zwitterionic moiety to form a 3-dimensional crosslinked polymer network; and contacting the crosslinked polymer network with a solution of a biologically active compound under conditions such that the biologically active compound is sequestered in the crosslinked polymer network.

DETAILED DESCRIPTION OF THE INVENTION

The invention provides a novel approach in which zwitterionic networks are used to sequester and deliver ionic biomolecules, such as proteins, without compromising their native conformation and bioactivity. Zwitterionic networks are designed to effectively retain and deliver ionic or polar biomolecules for guided tissue regeneration. The invention represents a conceptual advance and enables a novel strategy for the utilization of zwitterionic motifs as therapeutics delivery vehicles and tissue engineering scaffolds.

In contrast to the conventional narrow perception and categorization of zwitterionic materials as low-fouling and bioinert, the invention greatly expands the utilities of zwitterionic materials in the bioengineering and therapeutic areas. Zwitterionic networks are demonstrated as effective and versatile vehicles for engineering controlled bioactive microenvironment for biomedical applications. The invention distinguishes zwitterionic materials from the current benchmark biocompatible and anti-fouling material poly (ethylene glycol) (PEG) that is widely used in the biomaterials field. As demonstrated herein, the ability of the zwitterionic hydrogel to promote the functional bone healing with an exceptionally low dose of therapeutic proteins can significantly reduce the cost and improve the safety associated with the protein therapeutics.

For example, as disclosed herein, 3-dimensionally (3D) presented zwitterionic motifs (e.g., in crosslinked hydrogels), effectively sequestered osteogenic bone morphogenetic protein-2 (rhBMP-2). The ionic interactions between rhBMP-2 and the 3D zwitterionic network enabled dynamic sequestering and sustained release of the protein with preserved bioactivity. The zwitterionic hydrogel allowed high-efficiency in vivo local delivery of rhBMP-2, which can template the functional healing of critical-size femoral segmental defects in rats with rhBMP-2 at a loading dose substantially lower than those required for current natural or synthetic polymeric carriers. The sequestered rhBMP-2 can be sustainedly released well over a week with well-preserved bioactivity, driven by the dynamic ionic interactions of rhBMP-2 with the 3-dimensionally presented zwitterionic motifs rather than by scaffold biodegradations.

Such sequestration and high-efficiency delivery of rhBMP-2 allowed robust repair of critical-size rat femoral segmental defects templated by the zwitterionic hydrogel implant at an exceptionally low loading dose of 500-ng rhBMP-2.

Figure 1:
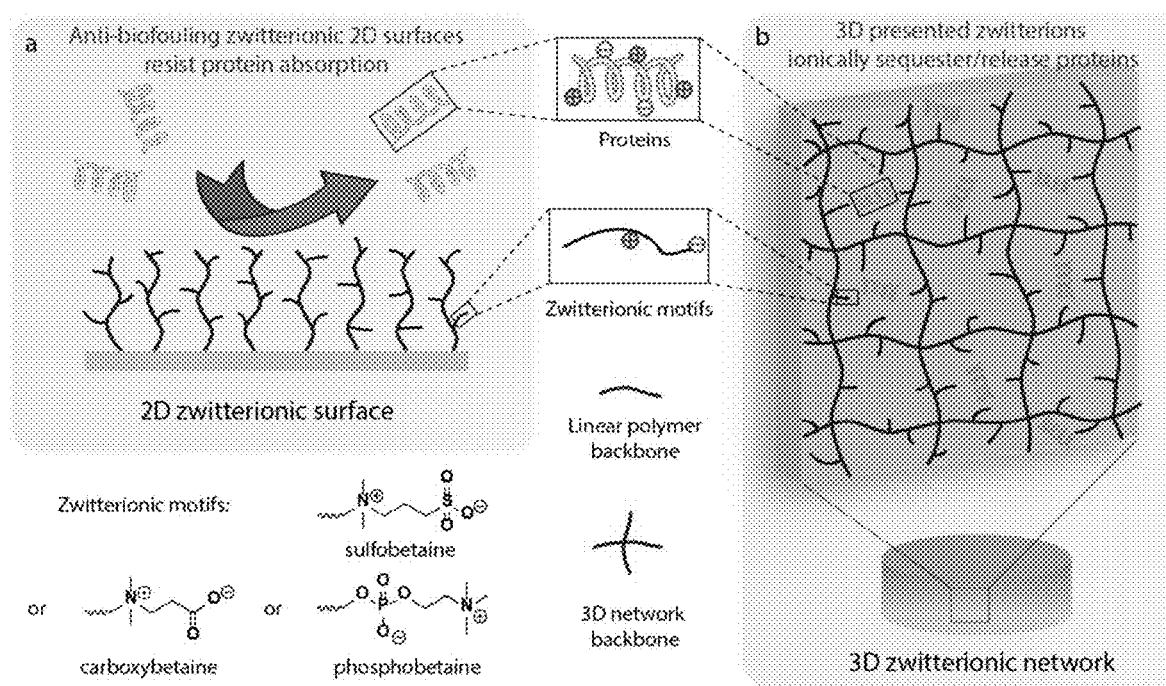
FIG. 1. Schematic illustrations of (a), the well-established anti-biofouling property of 2D zwitterionic surfaces vs (b), hypothesized protein-sequestering property of 3D zwitterionic networks.
Figure 5:
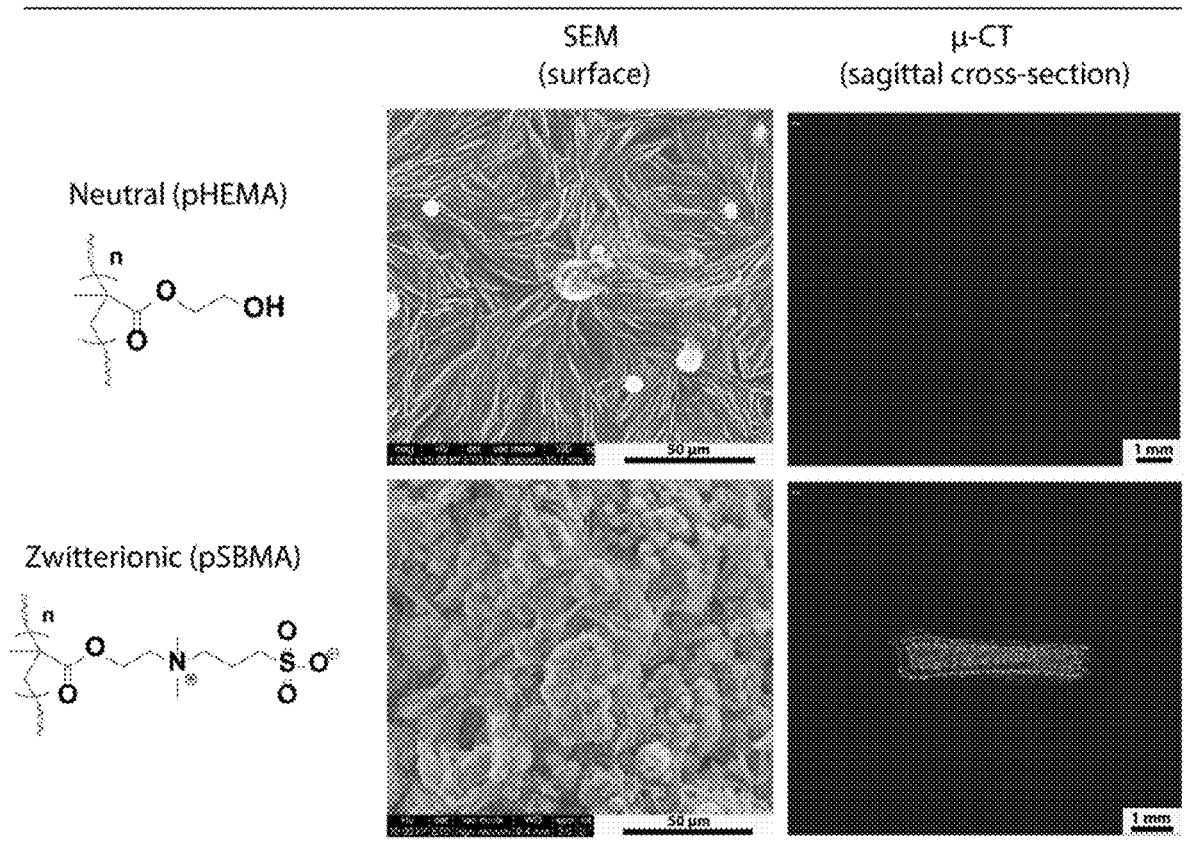
FIG. 5. Mineralization outcomes of zwitterionic pSBMA vs non-ionic pHEMA hydrogels as examined by SEM and CT. All hydrogels were crosslinked by 1.33 mol % of EGDMA relative to monomers. The hydrogels were placed in an aqueous acidic solution of hydroxyapaptite (pH=2.5-3.0, 14.7 mg/mL) containing 2-M urea, and subjected to controlled heating from 37° C. to 95° C. at 0.2° C./min. In the absence of ionic motifs, the mineralization of the non-ionic pHEMA hydrogel occurred exclusively on the surface. With both positive and negative charged residues facilitating the penetration of oppositely charged mineralization precursor ions (e.g. $Ca_2^{2+}$, $PO_4^{3-}$) across the hydrogel, the zwitterionic pSBMA templated extensive mineralization throughout the 3D hydrogel.

Zwitterions (e.g., phosphobetaine, sulfobetaine, and carboxybetaine) are well known for their anti-biofouling properties as widely demonstrated on 2-dimensional (2D) surfaces (FIG. 1a). The unique zwitterionic structures, simultaneously possessing cationic and anionic residues yet overall electronic neutral, exhibit strong affinity for water, thereby giving rise to super hydrophilic surfaces suppressing the hydrophobic interactions known to denature proteins. Zwitterionic sublfobetaine hydrogel have been reported to facilitate templated biomineralization was reported, which capitalizes on the ability of the zwitterionic motifs to effectively recruit/nucleate oppositely charged mineralization precursor ions (e.g., $Ca^{2+}$, $PO_4^{3-}$) across the 3D hydrogel network. (Liu, et al. 2013 Biomaterials 34:2442-54.) Unlike non-ionic hydrogel that was only able to template the mineralization on the surface, the zwitterionic hydrogel enabled extensive mineralization throughout the 3D network, supporting the critical role of zwitterionic motifs in recruiting precursor ions (FIG. 5). Prior to the disclosure herein, there has been no report on whether 3D zwitterionic motifs can effectively sequester ionic biomacromolecules, such as protein, their effective retention and sustained release (FIG. 1b).

Effective Sequestration of Proteins by 3D Zwitterionic Hydrogels

As examples, simple crosslinked polymethacrylate hydrogels bearing zwitterionic side chains were prepared. The in vitro sequestration/release profile of osteogenic human recombinant bone morphogenetic protein-2 (rhBMP-2) from the zwitterionic hydrogels was investigated and compared with that of the non-ionic low-fouling poly(ethylene glycol) hydrogel control. The efficacy of a zwitterionic sulfobetaine hydrogel in delivering rhBMP-2 in vivo to promote the functional healing of critical-size (5-mm) femoral segmental defects in rats and endogenous cell attachment on the otherwise low-fouling implant was investigated.

Figure 6:
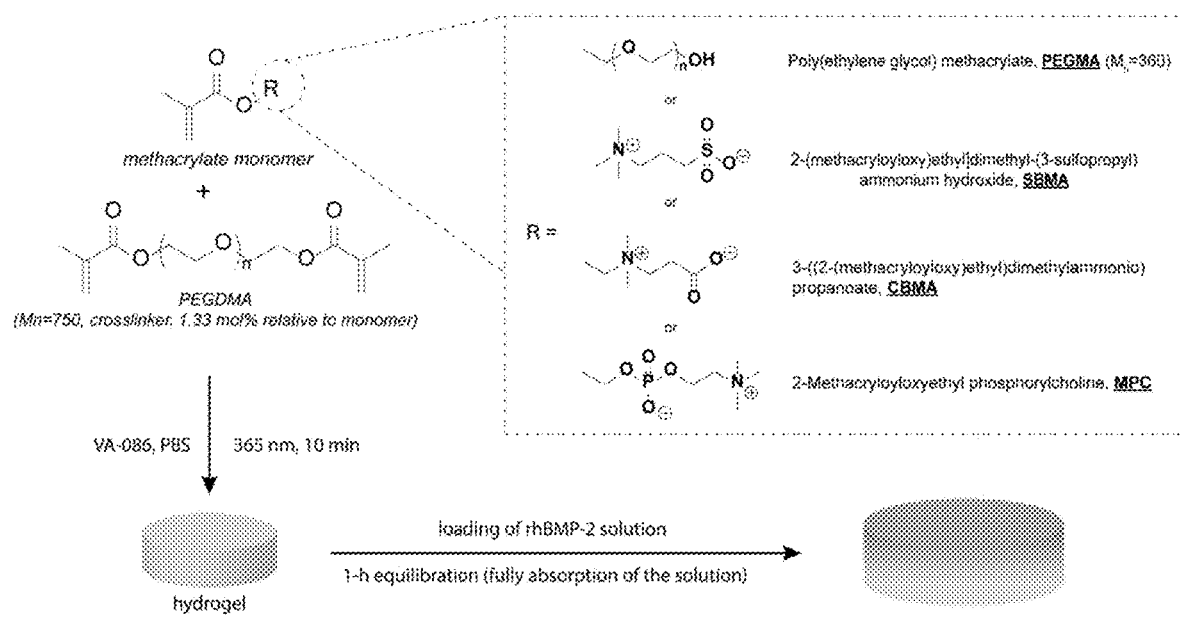
FIG. 6. Schematic illustration of the preparation of hydrogels from PEG and zwitterionic methacrylate monomers, and the loading of rhBMP-2 solutions on hydrogels though the de-swelling/swelling process. All hydrogels were prepared with identical crosslinker content of 1.33 mol % relative to monomers.

The zwitterionic PSBMA hydrogels were prepared by photo-crosslinking sulfobetaine methacrylate (SBMA) with varying contents of crosslinker PEGDMA. And a poly (ethylene glycol) methacrylate (PEGMA) hydrogels bearing non-ionic poly(ethylene glycol) (PEG), another well-established anti-biofouling motif, were prepared at the identical crosslinker contents as controls (FIG. 6 & Table 1). To examine the efficiency of the hydrogels for sequestering therapeutic proteins, 300 ng of rhBMP-2 (in 10 μL PBS solution) was loaded on each partially dried hydrogel and allowed to equilibrate at 37° C. for 1 h to ensure complete absorption of the aqueous solution (FIG. 6).

TABLE 1

Formulations of the photo-crosslinked hydrogels with identical crosslinker content

| Monomer | Monomer amount (mmol) | Crosslinker amount [a] (μL) | VA-086 stock solution [b] (μL) | PBS (μL) |
|---|---|---|---|---|
| SBMA | 2 | 17.9 | 100 | 1882.1 |
| PEGMA | 2 | 17.9 | 100 | 1882.1 |
| MPC | 2 | 17.9 | 100 | 1882.1 |
| CBMA | 2 | 17.9 | 100 | 1882.1 |

[a] PEGDMA ($M_n$ = 750).
[b] 2% (w/v) VA-086 in PBS.

Figure 2:
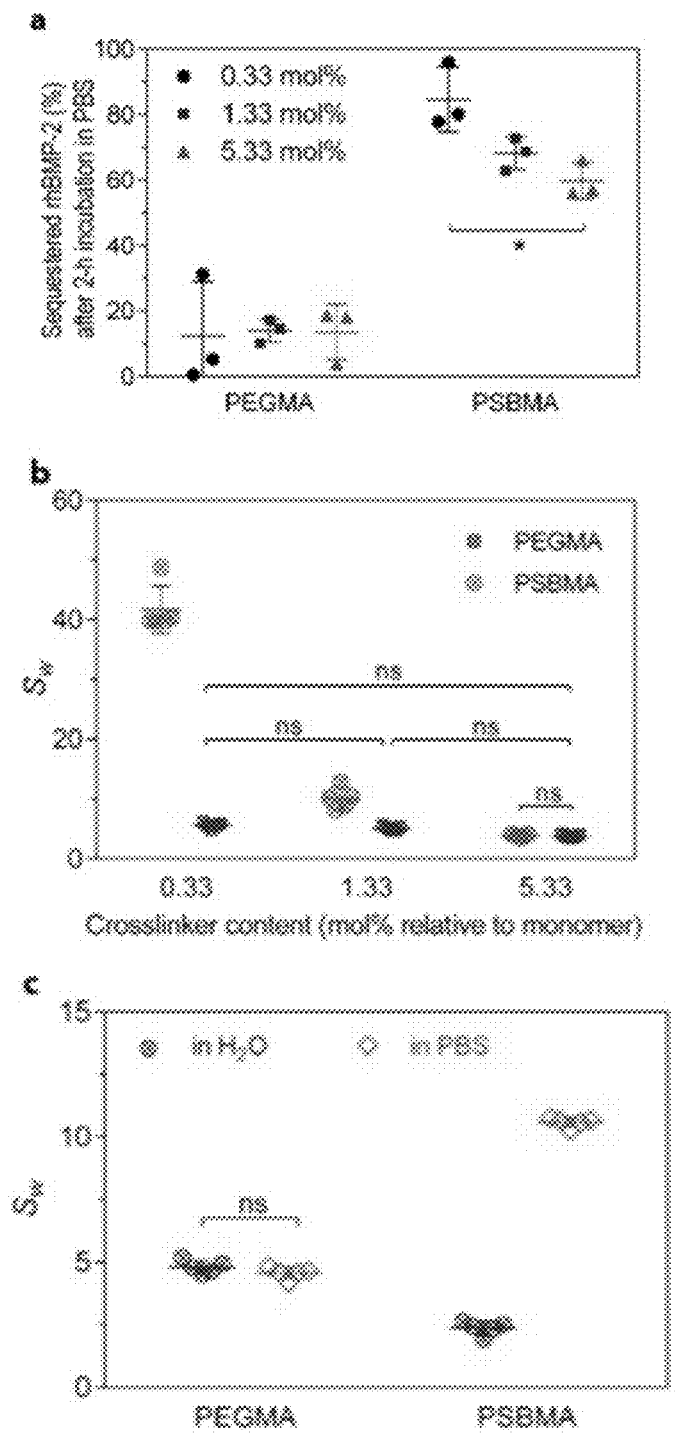
FIG. 2. 3D zwitterionic hydrogel networks efficiently sequestered rhBMP-2 and enabled its sustained in vitro release. (a), Sequestration of rhBMP-2 by zwitterionic PSBMA vs non-ionic PEGMA control as a function of crosslinker content (n=3, 0.33, 1.33 or 5.33 mol % relative to monomers) after 2-h incubation in PBS. A 300-ng rhBMP-2 initial loading dose was applied to all hydrogels and the sequestered protein content was determined after 2-h incubation in PBS. (b), Swelling ratio by weight ($S_w$) of PSBMA vs PEGMA hydrogels (n=5) in PBS as a function of crosslinker content (0.33, 1.33 or 5.33 mol % relative to monomers). (c), Swelling ratio by weight ($S_w$) of PSBMA vs PEGMA hydrogels (1.33 mol % crosslinker content; n=5) in water and in PBS. (d), Cumulative release of the loaded 300-ng rhBMP-2 from three types of zwitterionic hydrogels with identical crosslinker amount of 1.33 mol % (n=3). (e), Osteogenic trans-differentiation of C2C12 cells induced by the rhBMP-2 sustained-released (between day 7 to day 9) from PSBMA vs PEGMA hydrogels as shown by the expression of osteogenic marker ALP (red stains). C2C12 culture directly supplemented with 300-ng rhBMP-2 without any hydrogel carrier served as a positive control.*$p<0.05$ (two-way ANOVA).
Figure 2:
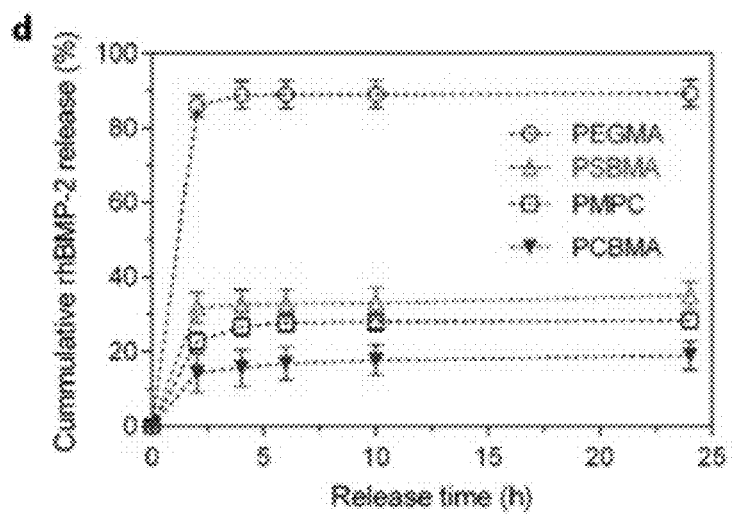
Figure 2:
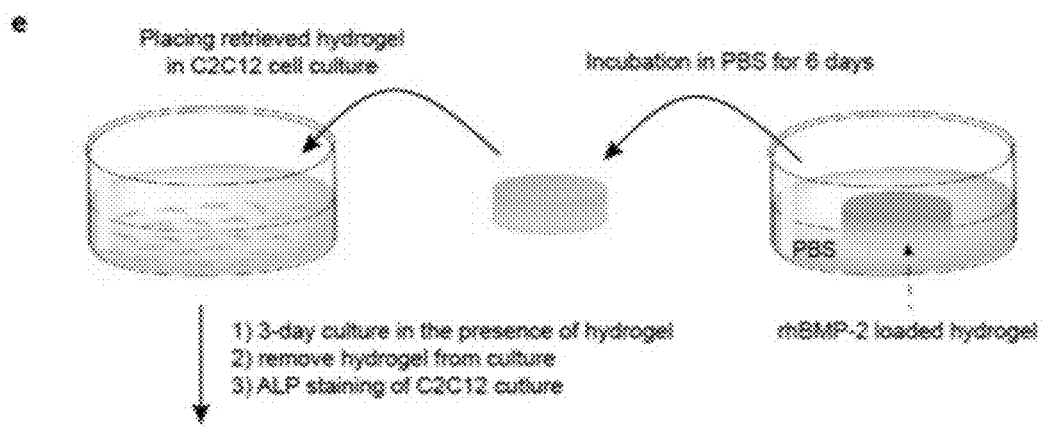
Figure 2:
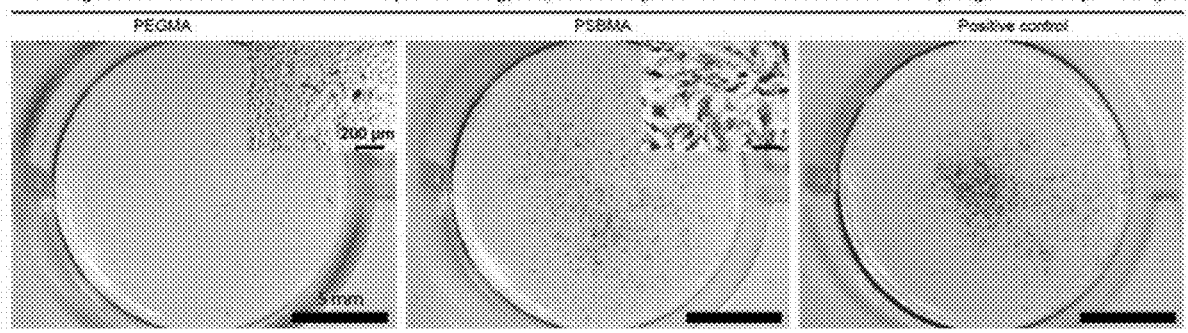

Although zwitterionic sulfobetaine and PEG surfaces are both known for resisting non-specific protein absorptions, the respective 3D networks exhibited significant differences in sequestering rhBMP-2 even with a similar swelling ratio at the identical crosslinker content of 5.33 mol % (relative to monomer; FIGS. 2a & 2b). The non-ionic PEGMA hydrogel could not effectively sequester rhBMP-2, with only about 10% of the initially loaded rhBMP-2 retained on the hydrogel after 2-h incubation in PBS (FIG. 2a). This observation is consistent with previous findings that PEG hydrogels lack affinity for ionic proteins. (Zhu 2010 Biomaterials 31:4639-56; Place, et al. 2009 Nature Materials 8:457-70.) By contrast, about 60% of the initially loaded rhBMP-2 was sequestered by the zwitterionic PSBMA network of the same crosslinker content (5.33 mol %) after 2-h incubation (FIG. 2a). Given the similar swelling ratio, thus similar diffusibility of solutes across the 3D network, the different efficiencies of sequestering ionic proteins observed with the two identically crosslinked networks was likely due to the different ionic states of their side chains. (Hoffman 2002 Advanced drug delivery reviews 54:3-12.)

Figure 7:
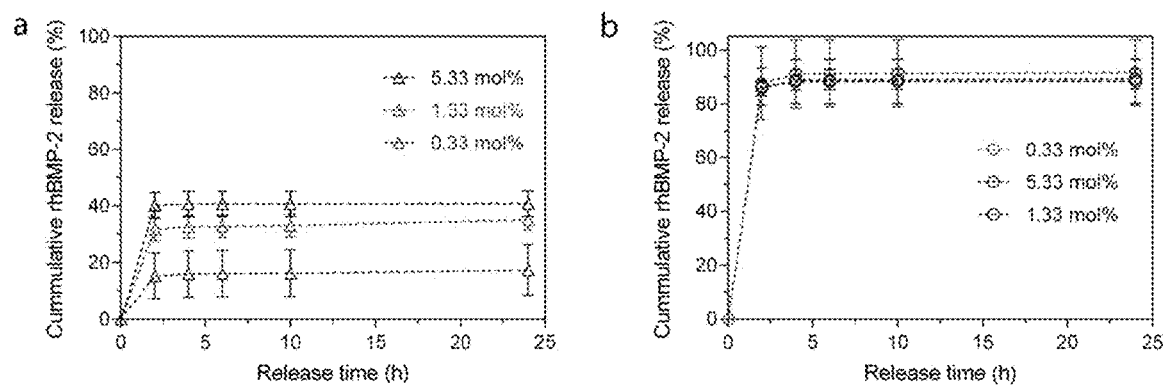
FIG. 7. Cumulative in vitro release of rhBMP-2 from (a) zwitterionic PSBMA and (b) non-ionic PEGMA hydrogels (n=3) as a function of PEGDMA crosslinker content in PBS (pH 7.4) as determined by the BMP-2 Quantikine kit (R&D Systems). Initial rhBMP-2 loading dose: 300 ng/hydrogel (cylindrical) specimen.

By reducing the degree of chemical crosslinking by up to 16-fold, it was shown that the zwitterionic PSBMA network swelled significantly in PBS by up to 10-fold while no significant crosslinker content-dependent changes in swelling ratio in PBS was observed with the non-ionic PEGMA network (FIG. 2b). This further supported that the different ionic states of side chains presented in the two 3D networks (zwitterionic vs non-ionic) can translate into significant differences in their physical properties in ionic environment, including different swelling behavior and efficiencies in sequestering/releasing ionic protein (FIGS. 2a and 7).

Figure 8:
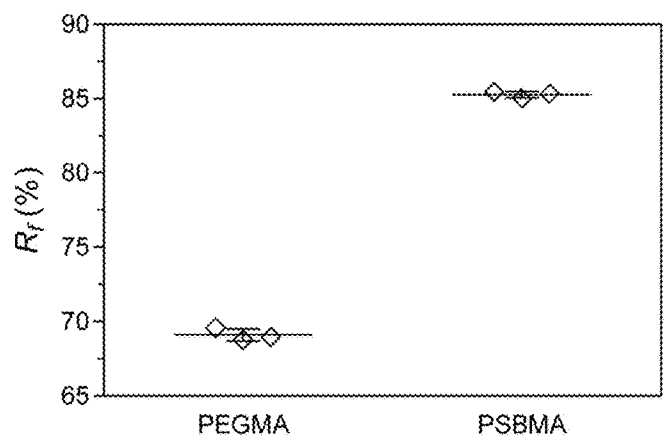
FIG. 8. Free water fraction ($R_f$) of PSBMA vs PEGMA hydrogels (n=3) equilibrated in PBS as determined by DSC. The difference between the two groups is significant ($p<0.05$, Student's T-test).

Furthermore, unlike the non-ionic PEGMA network that was insensitive to the presence of salts (no significant difference in swelling ratios in water vs in PBS, pH 7.4, FIG. 2c), the zwitterionic PSBMA network expanded almost 400% more in PBS than in water (FIG. 2b). Such an antipolyelectrolyte swelling behavior can be attributed to the disruption of the intermolecular salt bridges formed between the anionic sulfonate and cationic ammonium residues by ionic solutes. (Poynton, et al. 2002 *Spine* 27:S40-S8.) Combined with the higher free water fractions in the equilibrated zwitterionic PSBMA hydrogel (85% in PSBMA vs 69% in PEGMA, FIG. 8), this observation further supports that the ionic-sensitive nature of the zwitterionic network is beneficial to the diffusion of ionic solutes in general across the 3D network.

Taken together, these data validate that ionic interactions play an indispensable role in effectively sequestering rhBMP-2 by the zwitterionic PSBMA network. Similar rhBMP-2 retention profiles were also observed with the 3D zwitterionic networks bearing phosphobetaine (PMPC) and carboxybetaine (PCBMA) motifs (FIG. 2d), supporting effective protein retention as a novel yet generalizable feature for 3D zwitterionic matrices.

Sustained Release of Bioactive Proteins from Zwitterionic Hydrogels

Monitoring of the rhBMP-2 release from the hydrogels within the first 24 h of incubation in PBS by ELISA revealed ~30% release of the initially loaded protein in the first 2 h, followed by a 3% of slower release in the next 22 h (FIG. 2d), leaving >65% sequestered by the zwitterionic PSBMA (1.33 mol % crosslinker content) by 24 h.

To examine whether the rhBMP-2 sequestered by the PSBMA hydrogel could be continually released with retained bioactivity over a much longer period of time, an established culture model of BMP-2-induced osteogenic trans-differentiation of murine myoblast C2C12 cells was used. (Katagiri, et al. 1994 *J Cell Biol* 127:1755-66; Liu, et al. 2011 *Acta Biomaterialia* 7:3488-95.) This model was chosen over BMP-2-induced osteogenesis of mesenchymal stem cells (MSCs) due to the complete lack of expression of osteogneic markers by C2C12 cells prior to BMP-2 induction (thus much cleaner background than MSCs). It was shown that when the rhBMP-2-bearing PSBMA was placed in murine myoblast C2C12 culture after a 6-day pre-incubation in PBS, the further sustainedly released rhBMP-2 (from day 7 to day 9) from the PSBMA hydrogel was able to induce robust osteogenic trans-differentiation of C2C12 cells into alkaline phosphatase (ALP)-expressing osteoblasts (FIG. 2e). The intense ALP staining, comparable to that observed with the positive control culture (FIG. 2e) where 300-ng rhBMP-2 was directly supplemented without any carrier, suggest that the bioactivity of the sequestered and subsequently released rhBMP-2 was well preserved for at least 9 days.

This result is in stark contrast to the minimal ALP stains detected from the C2C12 culture supplemented with the PEGMA hydrogel subjected to identical BMP-2 loading and PBS pre-incubation treatment, consistent with the much poorer initial sequestration of rhBMP-2 by the non-ionic PEGMA hydrogel. It is worth noting that the circulation half-life of rhBMP-2 and most other growth factors, when in free form, tends to be very limited (e.g., 7-16 min for rhBMP-2). (Poynton, et al. 2002 *Spine* 27:S40-S8.) Here, well-preserved bioactivity of the rhBMP-2 sequestered by the PSBMA hydrogel was demonstrated well over a week. This may be attributed to the superhydrophilic structural water surrounding zwitterionic residues that prevent protein denaturing and the Hofmeister ions-like effect of the zwitterions for stabilizing native protein conformations. (Kane, et al. 2003 *Langmuir* 19:2388-91; Franz H. Zur Lehre von der Wirkung der Salze. Archiv für Experimentelle Pathologie and Pharmakologie 1888; 25; Keefe, et al. 2012 *Nat Chem* 4:60-4.) Overall, these observations support the zwitterionic PSBMA hydrogel as an effective carrier for the high-efficiency sequestration and sustained long-term release of therapeutic proteins such as rhBMP-2.

Treating Bone Defects by High-Efficiency In Vivo Delivery of Proteins

Figure 3:
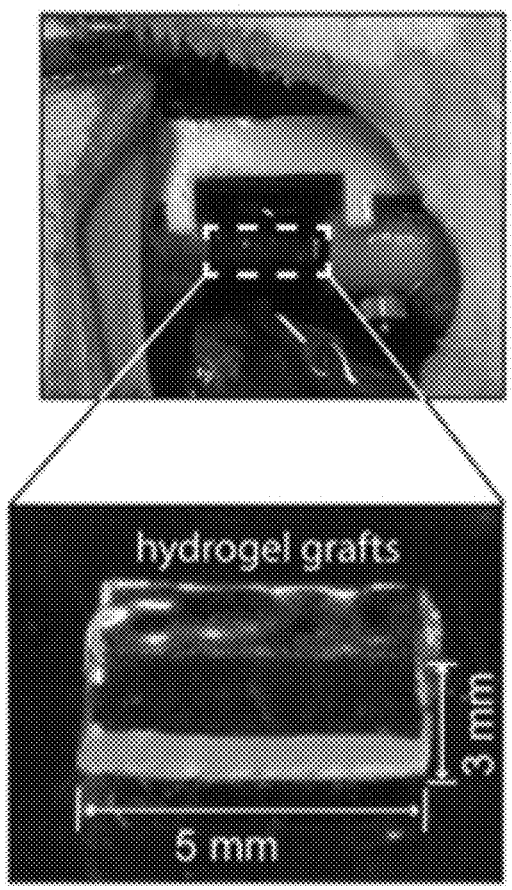
FIG. 3. High-efficient in vivo local delivery of rhBMP-2 by PSBMA hydrogel implant as examined by the 5-mm rat femoral segmental defect model. (a), A PSBMA hydrogel implant (5 mm×3 mm×3 mm) with/without rhBMP-2 press-fit within the femoral segmental defect stabilized by a radiolucent polyetheretherketone (PEEK) plate fixator. (b), Reconstructed μ-CT 3D images & 2D bone mineral density color mapping of the center longitudinal slice of the defect treated with PSBMA hydrogel grafts with/without 500-ng rhBMP-2 at 4 and 12 weeks post-op. (c), Bone volume & (d), Bone mineral density of the defects (n=4) treated with PSBMA hydrogel grafts with/without 500-ng rhBMP-2 at 4, 8 and 12 weeks post-op. *$p<0.05$ (two-way ANOVA) (e), Peak torque of the 12-week explants treated with PSBMA hydrogel grafts with/without rhBMP-2 (n=3) vs age-matched intact femurs (n=6). *$p<0.05$ (Student's T-test). (f), Reconstructed μ-CT 3D image & 2D bone mineral density color mapping of the center transverse slice of the defect treated with PSBMA hydrogel graft with 500-ng rhBMP-2 at 12 weeks post-op showing mature bony callus fully encapsulating the rhBMP-2 loaded PSBMA hydrogel scaffold. (g), H&E staining of the 12-week explant showing robust new bone (NB) fully encapsulating the rhBMP-2 loaded PSBMA scaffold and integrated with adjacent native cortical bone (CB). BM=bone marrow. Black arrows in the enlarged image denote hydrogel scaffolds integrated with the NB.
Figure 3:
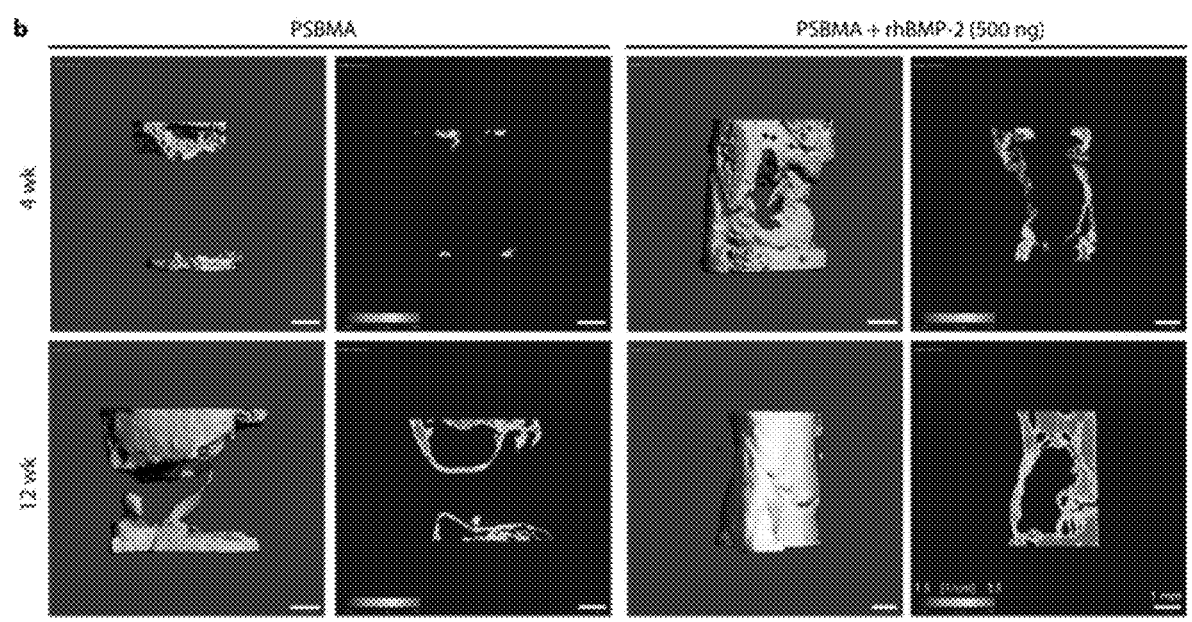
Figure 3:
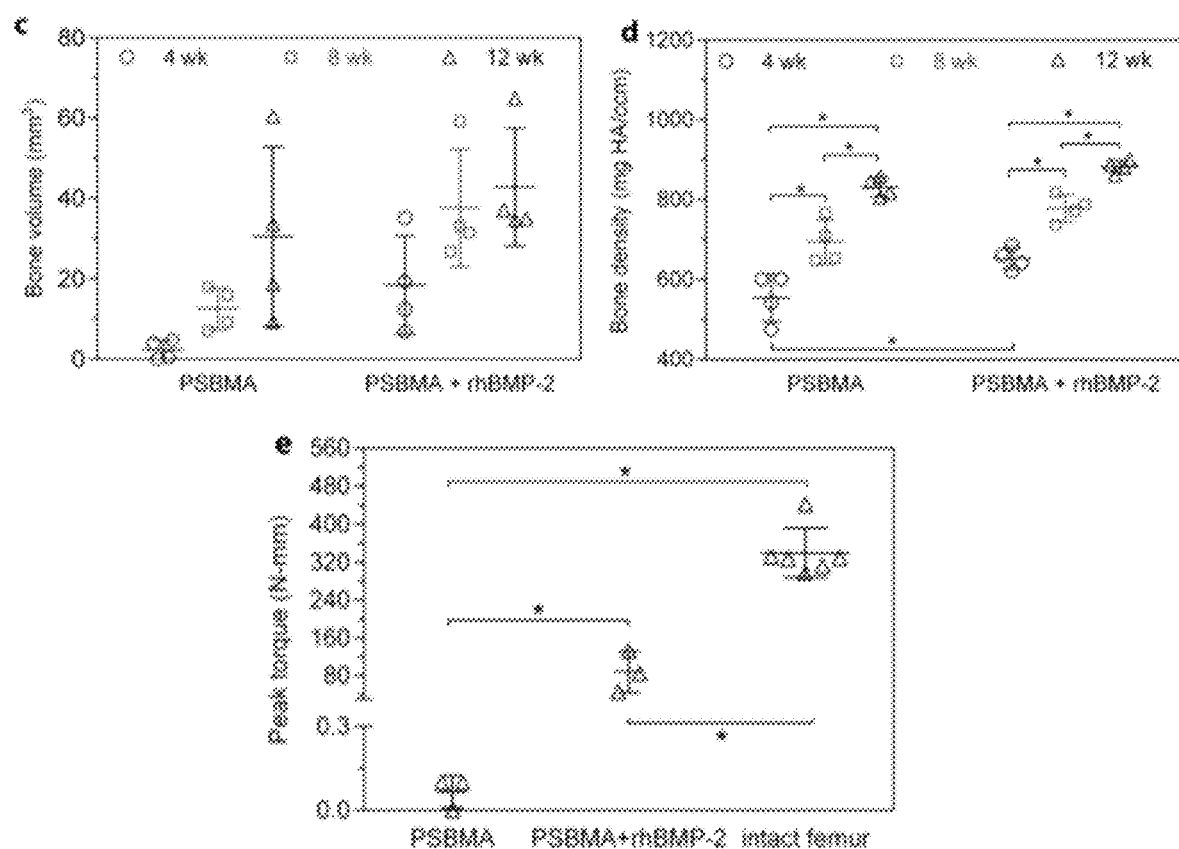
Figure 3:
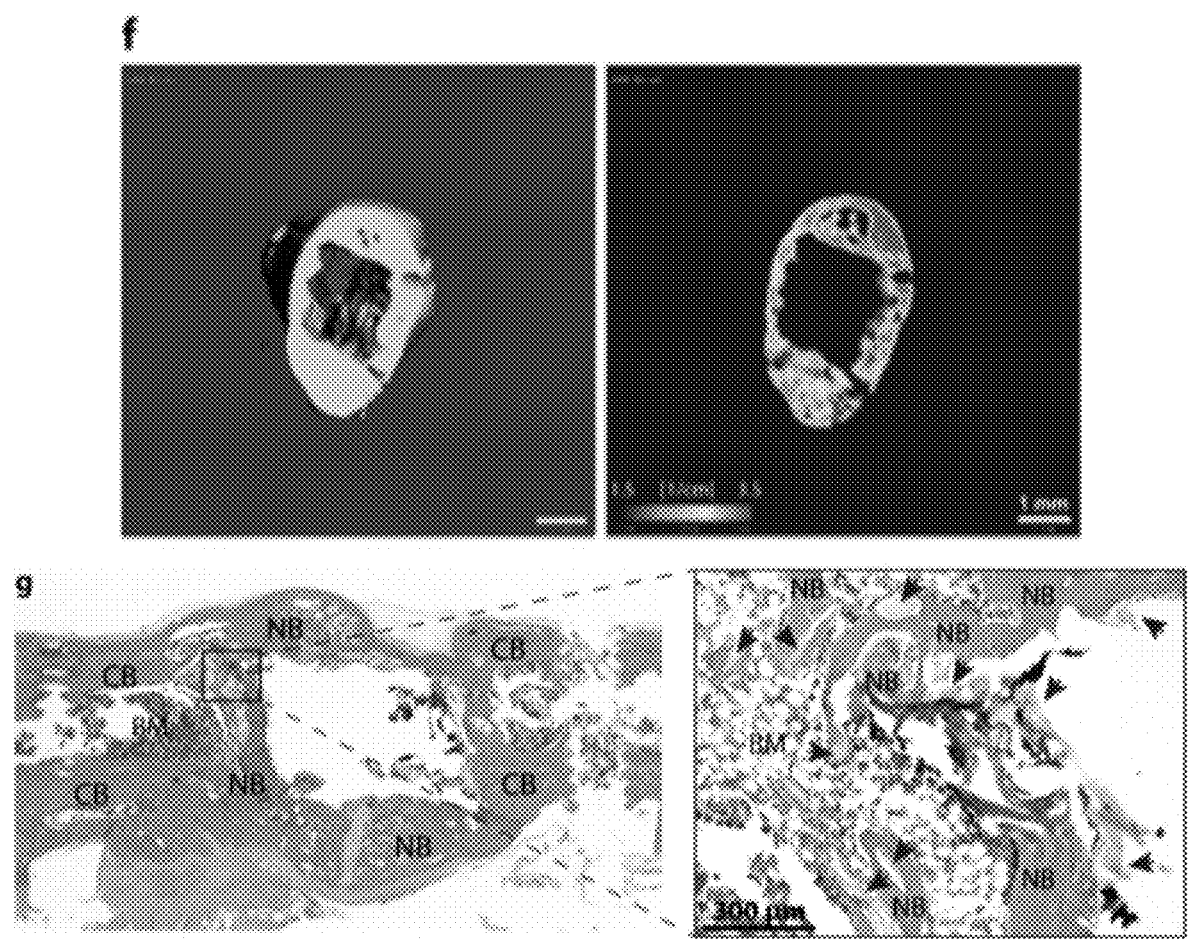

To test the in vivo efficacy of the PSBMA hydrogel as a synthetic implant with rhBMP-2 delivery capability, the repair of 5-mm rat femoral segmental defect, an established critical-size non-union model, templated by the PSBMA implant with or without pre-loaded rhBMP-2 was evaluated (FIG. 3a). (Filion, et al. 2011 *Tissue Eng Pt A* 17:503-11; Uhrig, et al. 2013 *Bone* 55:410-7.)

Current clinical use of rhBMP-2, delivered via absorbable collagen sponge carrier) (INFUSE®), to stimulate spine fusion or tibial fracture repair require exceedingly high loading doses comparable to ~1.5 mg per milliliter volume of defect (1500 ng/mm$^3$). Such a supra-physiological dosages and their burst release from the sub-optimal collagen carrier have resulted in significant systemic and local adverse effects. Loading doses ranging from 2 to 50-μg rhBMP-2/scaffold (~250 to 6,250 ng/mm-defect) have been typically used to achieve adequate repair of critical-size long bone or trabecular bone defects in rats with either natural or synthetic polymeric carriers. Table 2 lists representative reported rhBMP-2 loading doses on various natural or synthetic polymeric scaffolds used for achieving adequate healing of critical-size bone defects in rats. Literatures reporting synergistic loading of rhBMP-2 along with other growth factors/therapeutics are not included.

TABLE 2

Representative literature rhBMP-2 loading doses on various natural or synthetic polymeric scaffolds

| Scaffold type | Scaffold materials | Defect model | rhBMP-2 loading dose | | |
|---|---|---|---|---|---|
| | | | μg/ scaffold | μg/mm-defect | μg/mm$^3$ |
| Natural | Collagen (INFUSE ®)$^a$ | 6-mm segmental, ulna | 3 | 0.5 | 1.5 |
| | Gelatin Alginate | 8-mm segmental, femur | 2 | 0.25 | |
| | | | 5 | 0.63 | |
| | Keratose | 8-mm segmental, femur | 50 | 6.25 | |
| | Silk | 5-mm segmental, femur | 2.5 | 0.5 | |
| | Hyaluronic acid | 5-mm cranium | 5 | | |
| Synthetic | PPF/TCP | 5-mm segmental, femur | 10 | 2 | |
| | PLGA & PPF | 5-mm segmental, femur | 6.5 | 1.3 | |
| | PLA-DX-PEG | 4-mm, ilia | 10 | | |
| | PEG-RGD | 8-mm, cranium | 5 | | |
| | PSBMA$^b$ | 5-mm segmental, femur | 0.5 | 0.1 | 0.01 |

$^a$ commercial rhBMP-2 delivery scaffolds approved by FDA.
$^b$ zwitterionic PSBMA hydrogel scaffold used in the current study.
"*" References: Mckay, et al. 2007 Int'l orthopaedics 31: 729-34; Carragee, et al. 2011 Spine J 11: 471-91; Ratanavaraporn, et al. 2011 Biomaterials 32: 2797-811; Kolambkar, et al. 2011 Bone 49: 485-92; de Guzman, et al. 2013 Biomaterials 34: 1644-56; Kirker-Head, et al. 2007 Bone 41: 247-55; Patterson, et al. 2010 Biomaterials 31: 6772-81; Kempen, et al. 2009 Biomaterials 30: 2816-25; Lutolf, et al. 2003 Nat Biotechnol 21: 513-8; Chu, et al. 2007 Biomaterials 28: 459-67; et al. 2001 Nat Biotechnol 19: 332-5.

Loading doses of rhBMP-2 less than 2 (without synergistic delivery of other growth factor therapeutics) often resulted in inadequate/inconsistent repair outcomes.

(Schmoekel, et al. 2005 *Biotech. & bioeng.* 89:253-62.) Here, in contrast, a significantly lower loading dose of 500-ng rhBMP-2 was applied to the PSBMA scaffold (equivalent to ~11 ng/mm$^3$ or 100 ng/mm-defect) press-fit into the 5-mm rat femoral segmental defect. It is believed that consistent functional healing of critical rat long bone defect with such a low loading dose of rhBMP-2 alone has never been reported before.

Figure 9:
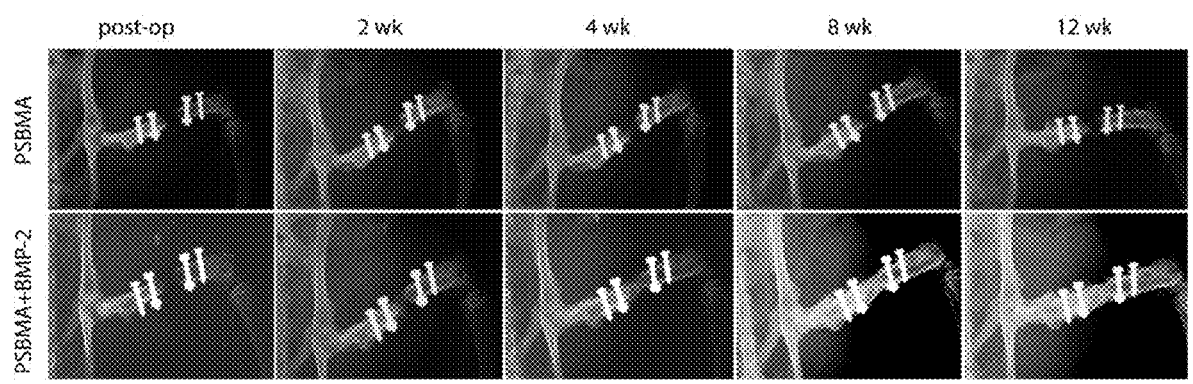
FIG. 9. Radiographic monitoring over time of the bony callus formation over the 5-mm rat femoral segmental defects treated with PSBMA hydrogel grafts with/without 500-ng rhBMP-2.
Figure 10:
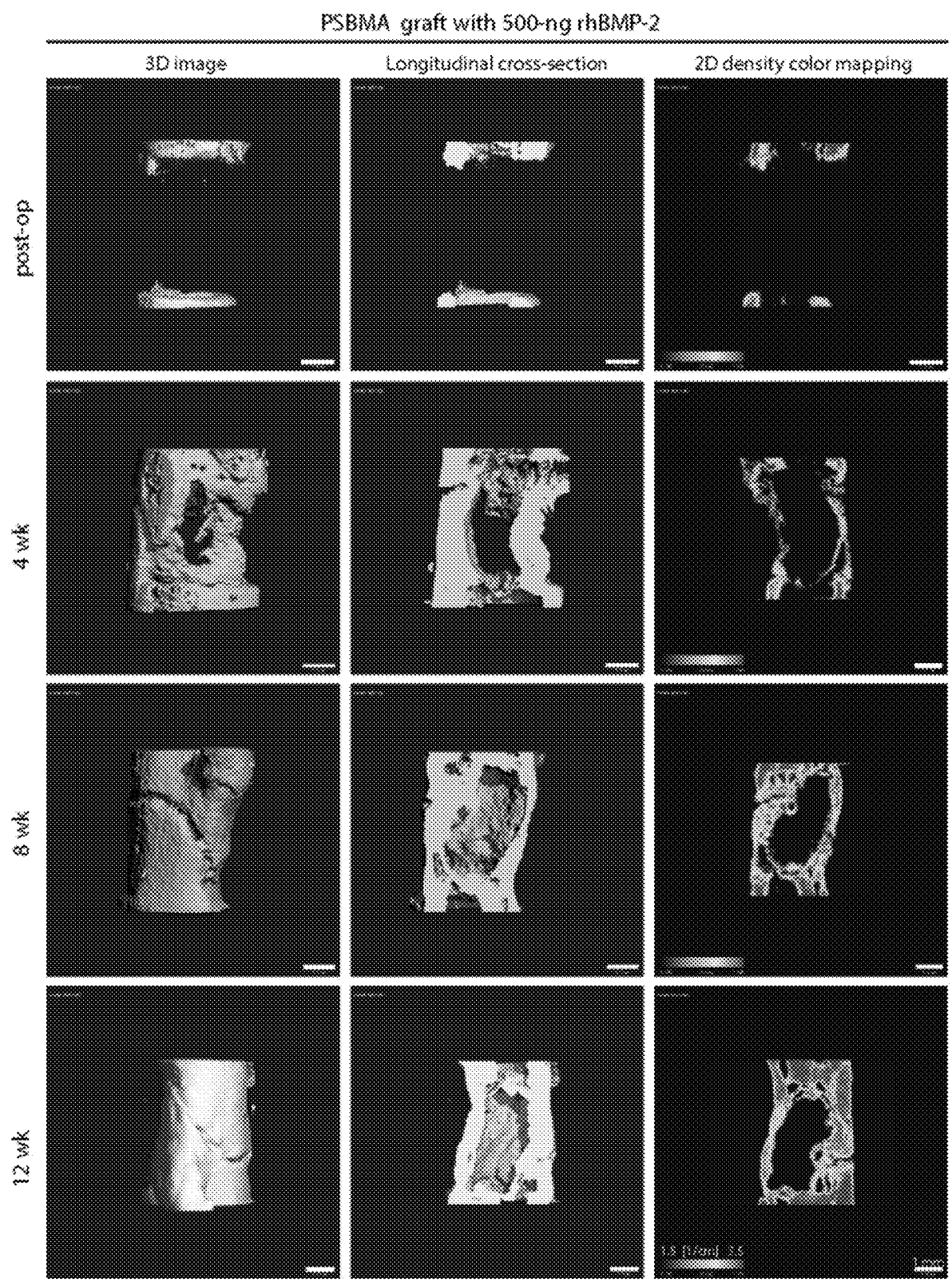
FIG. 10. Reconstructed μ-CT 3D images, longitudinal cross-section views, and longitudinal 2D bone mineral density color mapping of the 5-mm femoral segmental defect treated with PSBMA hydrogel grafts with 500-ng rhBMP-2 over time.
Figure 11:
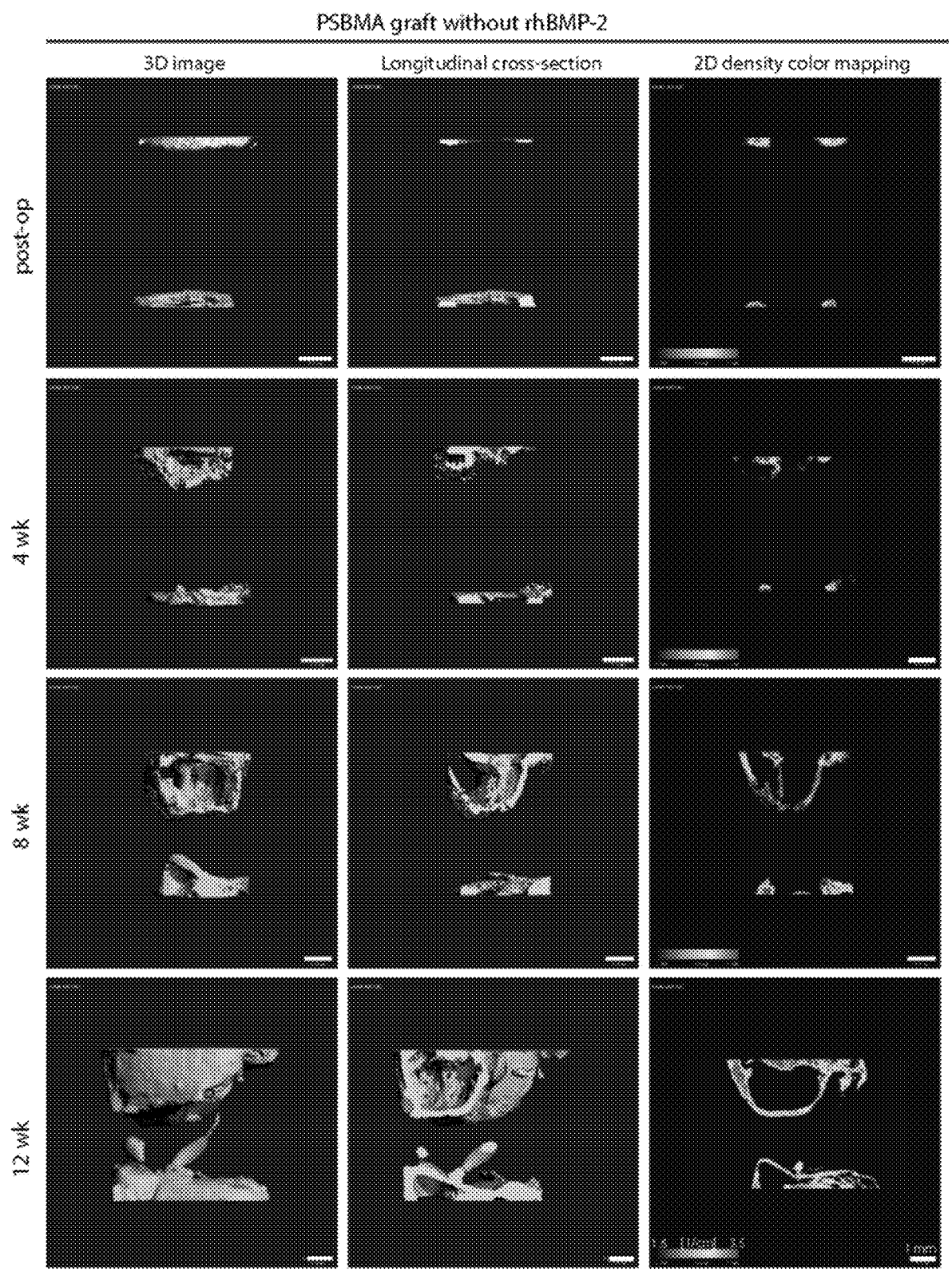
FIG. 11. Reconstructed μ-CT 3D images, longitudinal cross-section views, and longitudinal 2D bone mineral density color mapping of the 5-mm femoral segmental defect treated with PSBMA hydrogel grafts alone over time.

At 2 weeks, mineralized healing callus emerged around the defects implanted with PSBMA with rhBMP-2 (FIG. 9). Strikingly, the bony callus started to bridge over the defect by as early as 4 weeks (FIG. 3*b*, FIG. 10), and by 12 weeks, mature and uniform bony callus characterized with recanalization and high bone mineral density (FIGS. 3*b*, 3*d*, 3*f*, FIG. 10) fully encapsulated the defect, leading to substantial restoration (~40% compared to intact age matched femur control) of the torsional rigidity of the defect (FIG. 3*e*).

Figure 12:
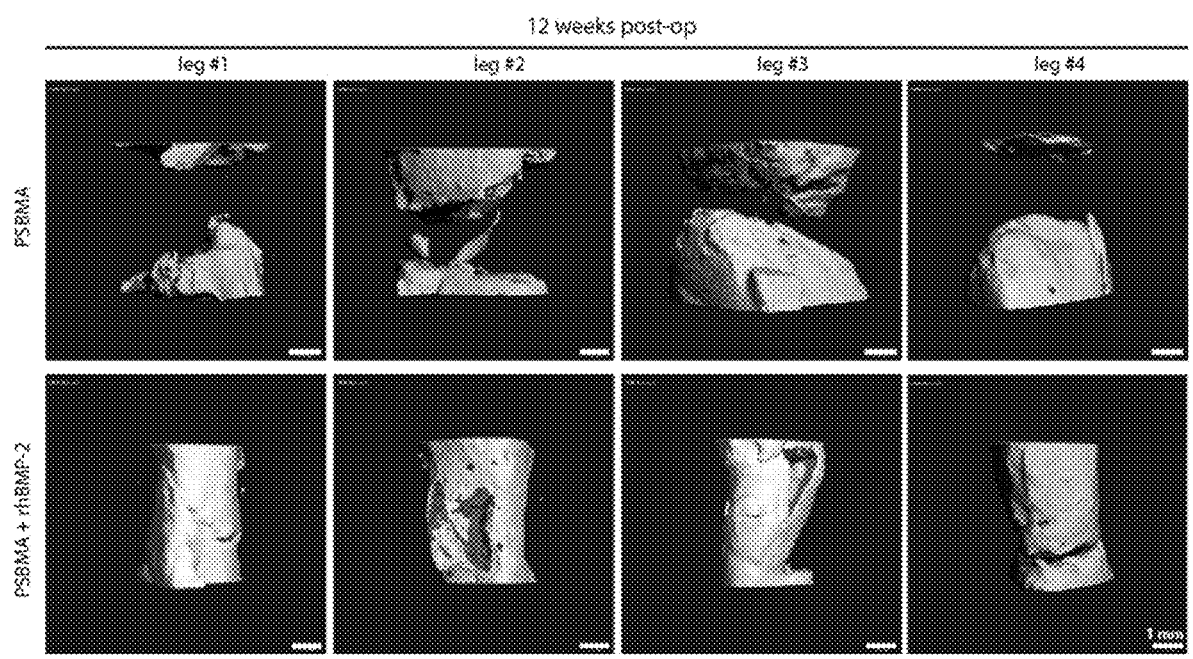
FIG. 12. Reconstructed μ-CT 3D images of all 5-mm femoral segmental defects treated with PSBMA hydrogel implants with/without the loading of 500-ng rhBMP-2 at 12 weeks post-op.

Continued remodeling of the new bone is expected to further increase the torsional rigidity over time. In the absence of rhBMP-2, the PSBMA also led to the early onset (FIG. 9) and steady growth of bony callus over the course of 12 weeks as characterized with increasing bone volume (FIG. 3*c*) and bone mineral density (FIG. 3*d*). However, in the absence of rhBMP-2, the calcified callus failed to bridge over the entire defects by 12 weeks (FIGS. 3*b*, 9, 11 & 12) to restore the biomechanical integrity of the defect (FIG. 3*e*). Of note, although fairly high bone volumes were detected at the regions of interest (ROI) in both treatment groups by 12 weeks (FIG. 3*c*, no statistically significant difference), the rhBMP-2 treated group consistently guided uniform bony callus formation across the full length of the defect whereas the new bone formation templated by the no-BMP-2 control group was primarily localized around the graft-cortical bone junctions (FIG. 12).

Transverse cross-sectional view of the repaired defect (FIG. 3*f*) and H&E staining of the explant at 12-week post-op (FIG. 3*g*) revealed that the bony callus formation was tightly templated by and integrated with the PSBMA hydrogel (note that the disintegration/shrinkage of hydrogel scaffold trapped within the bony callus was a histology processing artifact as the hydrogel shrank dramatically upon dehydration).

These data supported that PSBMA hydrogel implant is a highly effective carrier for the local delivery of rhBMP-2, which enabled the functional repair of rat critical-size long bone defect at a significantly reduced BMP-2 loading dose that is desired from both safety and cost-effectiveness perspectives.

rhBMP-2 Sequestration Promoting Endogenous Cell Attachment & ECM Deposition on the Otherwise Low-Fouling Surface of Zwitterionic PSBMA Hydrogel Implant The robust early bone healing enabled by PSBMA in the presence of rhBMP-2 across the entire defect suggests that a cascade of cellular events required for initiating bone healing must have occurred in a timely manner along the implant surface, counterintuitive to the perception that zwitterionic surfaces and scaffolds tend to reduce protein absorptions/cellular adhesion. (Smith, et al. 2012 *Sci Transl Med* 4, 153; Zhang, et al. 2013 *Nat Biotechnol* 31:553-6; Bose, et al. 2012 Trends in biotechnology 30:546-54; Liu, et al. 2009 *Biomacromol.* 10:2809-16.)

Figure 4:
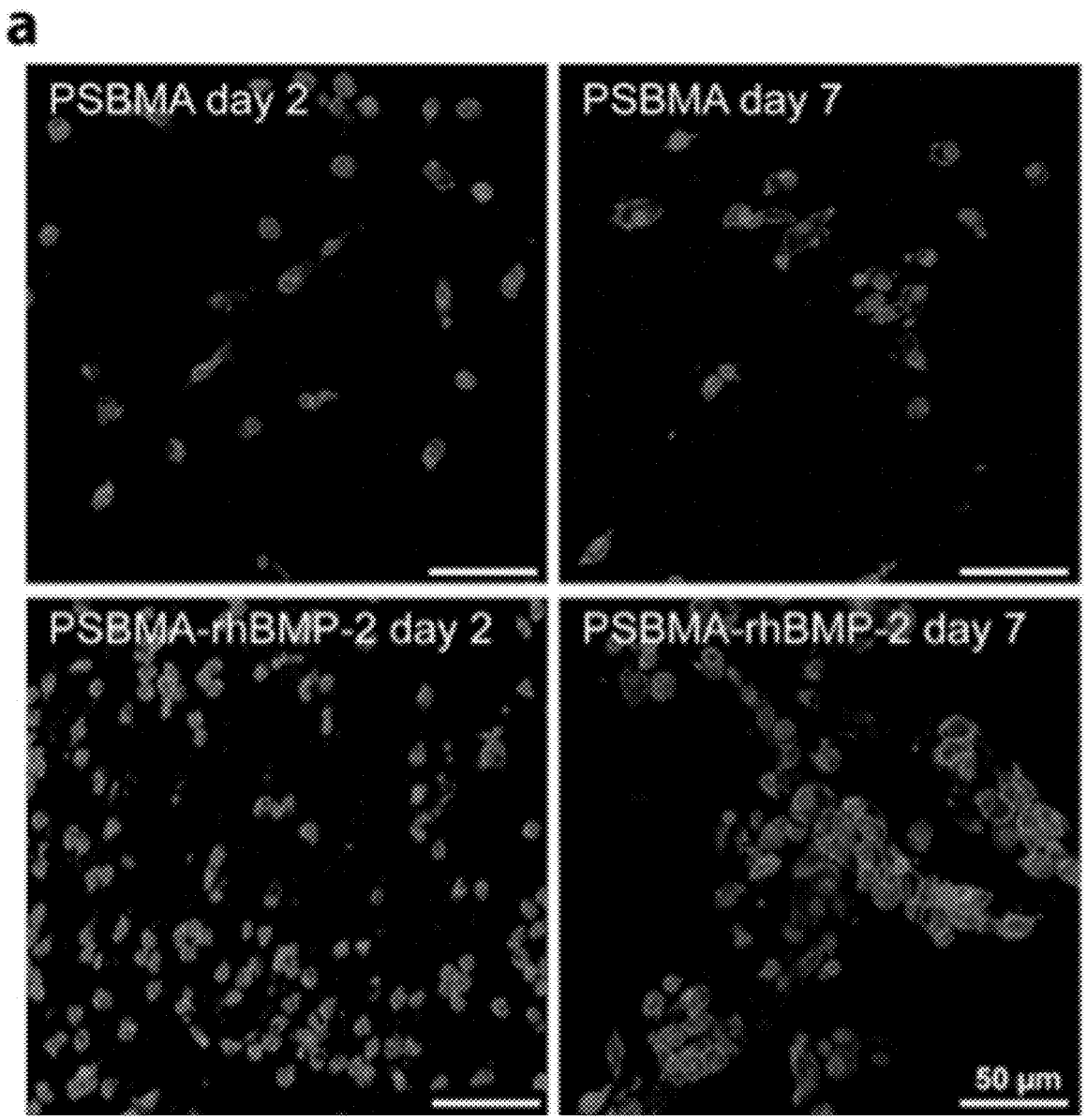
FIG. 4. Temporally sequestered rhBMP-2 increased the cell attachment & ECM deposition on the low-fouling zwitterionic PSBMA hydrogel implant. (a), Confocal images of in vivo endogenous cell attachment on the surface of PSBMA explants with/without rhBMP-2 at day 2 and 7 post-op. Actin was stained by Alexa phalloidin (red) while nuclei were stained by DAPI (blue). (b), H&E staining of the ECM deposition on the explants with/without rhBMP-2 at day 2 and 7 post-op.
Figure 4:
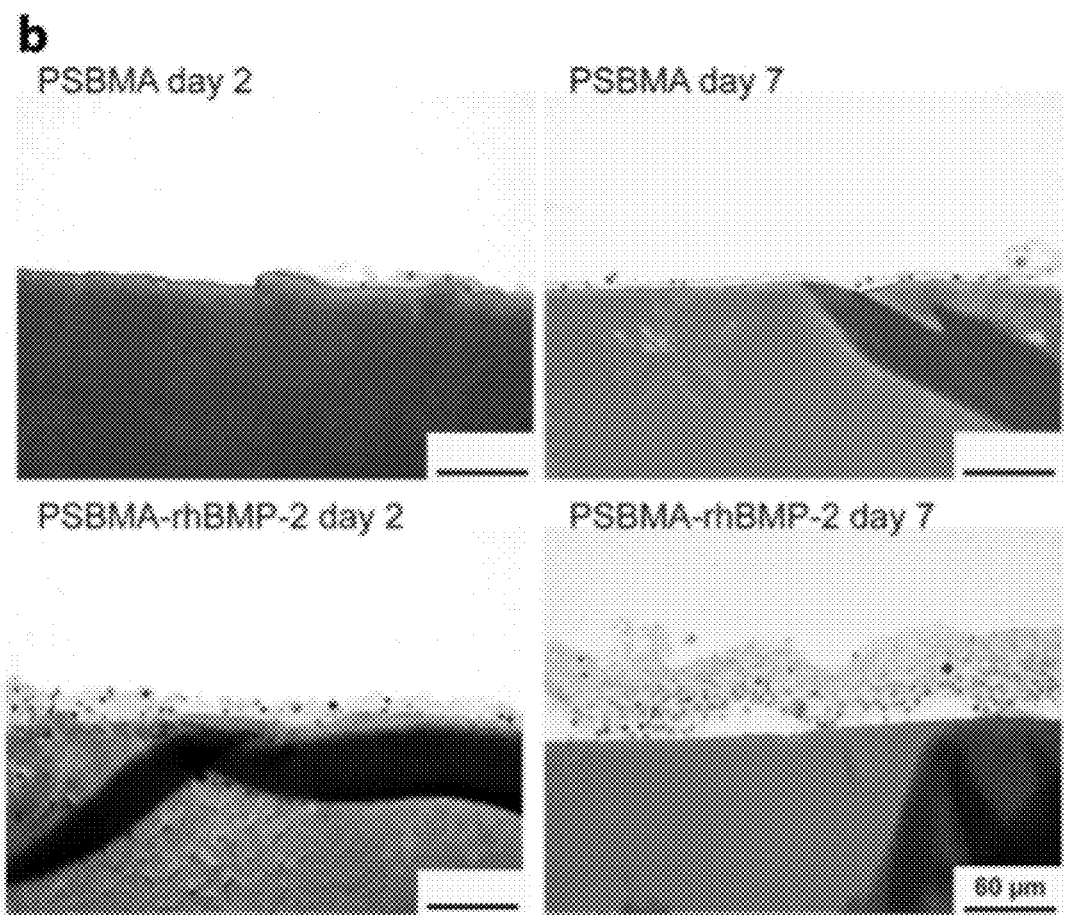

Also investigated was the early stage in vivo cell attachment during the guided bone healing with and without the loading of rhBMP-2. The results showed that the retention of rhBMP-2 by the PSBMA hydrogel implants shifted the microenvironment of the zwitterionic scaffolds from low-fouling to cell adhesive. As revealed by fluorescent microscopy and H&E staining, only limited cell attachment was observed on the surface of the PSBMA hydrogel without rhBMP-2 within the first 2 days post-implantation with no obvious increases by 7 days (FIG. 4). This is consistent with the low-fouling nature of zwitterionic surfaces as well as the recent report that zwitterionic carboxybetaine hydrogels suppressed fibrous tissue encapsulation in vivo. (Zhang, et al. 2013 *Nat Biotechnol* 31:553-6)

In contrast, substantially more endogenous cells attached to the surface of the rhBMP-2-bearing PSBMA implant at 2 days post-implantation (FIG. 4), and these adherent cells continued to proliferate and led to more effective ECM deposition, and presumably the initiation of callus formation, at day 7 post-implantation. These observations suggest that the ionic retention of rhBMP-2 on the 3D zwitterionic scaffold not only introduced osteoinductivity, but also improved the osteoconductivity of the otherwise commonly perceived low-fouling and bioinert scaffold, enabling facile cellular attachment. As many ECM components such as fibronectin, collagen and laminin have high affinity for heparin-binding growth factors like BMPs, the rhBMP-2-bearing scaffold in turn could facilitate the attachment of these ECM components and subsequent cellular adhesion and more uniform and robust bony callus formation. (Ruoslahti, et al. 1991 *Cell* 64:867-9.)

Thus, in one aspect, the invention generally relates to a composite material comprising a polymer network and a biologically active compound, wherein the 3-dimensional polymer network comprises a zwitterionic moiety.

In certain embodiments, the biologically active compound is a biomacromolecule. In certain embodiments, the biologically active compound is a small molecule compound. In certain embodiments, the biologically active compound is a biomacromolecule such as an ionic or polar protein or peptide.

In certain preferred embodiments, the biomacromolecule is a therapeutic osteogenic protein, an anabolic agent or any angiogenic factor, for example, selected from BMPs (e.g., rhBMP-2, rhBMP-7, rhBMP-2/7 heterodimer), TGF-beta, EGF, FGF, IGF-1, and VEGF. In certain embodiments, the therapeutic osteogenic protein is present in the polymer network at a loading from about 1 ng to about 20,000 ng (e.g., from about 1 ng to about 20,000 ng, from about 10 ng to about 20,000 ng, from about 100 ng to about 20,000 ng, from about 1,000 ng to about 20,000 ng, from about 5,000 ng to about 20,000 ng, from about 10,000 ng to about 20,000 ng, from about 1 ng to about 10,000 ng, from about 1 ng to about 5,000 ng, from about 1 ng to about 3,000 ng, from about 1 ng to about 1,000 ng, from about 1 ng to about 500 ng, from about 1 ng to about 300 ng, from about 1 ng to about 100 ng) per critical-size femoral segmental defect (e.g., in rat or scaled to human defect sizes accordingly).

The polymer network is preferably a 3-dimensional cross-linked polymer network. Any suitable polymer network may be utilized, for example, a crosslinked hydrogel of polymethacrylate, polyacrylate, polymethacrylamide or polyacrylamide. Any suitable crosslinkers may be utilized, for example, selected from poly(ethylene glycol) dimethacrylate, poly(ethylene glycol) diacrylate, ethylene glycol diacrylate and ethylene glycol dimethacrylate, or derivatives thereof (e.g., amides). The polymer network may be crosslinked to any suitable crosslinking density, for example, from about 0.05 mol % to about 10 mol % (e.g., from about 0.05 mol % to about 5 mol %, from about 0.05 mol % to about 3 mol %, from about 0.05 mol % to about 1 mol %, from about 0.05 mol % to about 0.5 mol %, from about 0.05 mol % to about 0.1 mol %, from about 0.1 mol % to about 10 mol %, from about 0.5 mol % to about 10 mol %, from about 1 mol % to about 10 mol %, from about 5 mol % to about 10 mol %).

Any suitable zwitterionic moieties may be incorporated in the polymer network, for example, one or more selected from sulfobetaine, phosphorylcholine and carboxybetaine. The zwitterionic moieties may be present in a polymer network in the backbone and/or as pendant groups to a polymeric backbone. The zwitterionic moieties may be present in the polymer network at any suitable density, for example, from about 1 mol % to about 100 mol % (e.g., from about 1 mol % to about 50 mol %, from about 1 mol % to about 30 mol %, from about 1 mol % to about 30 mol %, from about 1 mol % to about 10 mol %, from about 1 mol % to about 5 mol %, from about 5 mol % to about 100 mol %, from about 10 mol % to about 100 mol %, from about 30 mol % to about 100 mol %, from about 50 mol % to about 100 mol %).

In certain embodiments, the composite material is biodegradable.

In another aspect, the invention generally relates to an implant comprising a composite material characterized by a 3-dimensional crosslinked polymer network sequestered therein one or more biologically active compounds, wherein the polymer comprises a zwitterionic moiety.

In yet another aspect, the invention generally relates to an implant comprising a 3-dimensional scaffold comprising a 3-dimensional polymer network, wherein the polymer network comprises a zwitterionic moiety, adapted to sustained in vivo delivery of one or more biologically active compounds.

In yet another aspect, the invention generally relates to an implant comprising a n implant comprising a composite material characterized by a 3-dimensional crosslinked polymer network comprising a zwitterionic moiety.

In certain preferred embodiments, the implant of the invention is suitable for treating dental, bone, cartilage, tendon, ligament or osteochondral damage.

In yet another aspect, the invention generally relates to a method for making a composite material useful for tissue engineering. The method includes crosslinking, in the presence of a biologically active compound, a polymer comprising a zwitterionic moiety to form a 3-dimensional crosslinked polymer network with the biologically active compound encapsulated therein.

In yet another aspect, the invention generally relates to a method for making a composite material useful for tissue engineering. The method includes: crosslinking a polymer comprising a zwitterionic moiety to form a 3-dimensional crosslinked polymer network; and contacting the crosslinked polymer network with a solution of a biologically active compound under conditions such that the biologically active compound is sequestered in the crosslinked polymer network.

EXPERIMENTAL

Preparation of Hydrogels

Zwitterionic hydrogels poly[2-(methacryloyloxy)ethyl] dimethyl-(3-sulfopropyl)ammonium hydroxide (PSBMA), poly(2-Methacryloyloxyethyl phosphorylcholine) (PMPC), poly[3-((2-(methacryloyloxy)ethyl)dimethylammonio)propanoate] (PCBMA) and nonionic poly(ethylene glycol) methacrylate (PEGMA, Mn=360) were prepared (Table 1). Monomers SBMA, MPC and PEGMA (Mn=360) and crosslinker poly (ethylene glycol) dimethacrylate (PEGDMA, Mn=750) were purchased from Aldrich (St. Louis, Mo.), while CBMA was synthesized as reported. (Zhang, et al. 2006 Langmuir 22:10072-7.) The radical inhibitors in PEGMA and PEGDMA were removed by passing through an aluminum oxide column prior to use. In a typical procedure, 2 mmol respective monomer was combined with 17.9 µL of PEGDMA, 100 µL of PBS solution of 2,2'-Azobis[2-methyl-N-(2-hydroxyethyl)propionamide] (VA-086, 2%, w/v), and 1882.1 µL of PBS. The mixture was bath-sonicated, and sterilized by passing through 0.22-µm polyethersulfone (PES) membrane filter (Millipore). The resulting solution was transferred to a custom-made Teflon mold with cylindrical (6 mm in diameter, 50 µL/well), square prism (5 mm×5 mm, 50 µL/well) or rectangle (6.5×32.6 mm, 400 µL/well) wells and solidified under the irradiation of 365-nm light for 10 min in a sterile hood. The hydrogels were stored in sterile PBS until further uses.

Swelling Ratios of the Hydrogels

The swelling ratios by weight (Sw) of the hydrogels were determined in Milli-Q water or in PBS (pH=7.4) at room temperature according to Equation 1:

$$S_w = \frac{W_h - W_d}{W_h} \qquad \text{Eq-1}$$

where $W_h$ and $W_d$ are the weight of the hydrogel in fully hydrated state in water/PBS and freeze-dried state, respectively.

Free Water Fraction in the Hydrogels

The free water fraction in the hydrogels was measured by differential scanning calorimetry (DSC) on a Q200 Modulated DSC (TA Instruments). About 15 mg of hydrogel equilibrated either in water or PBS was placed in an aluminum pan. The pan was then sealed tightly to prevent water evaporation during the measurement. The testing was carried out from −40° C. to 40° C. at a heating rate of 2° C./min. The exothermal peak around 0° C., attributed to the melting of the free water[19], was calculated as $\Delta H_{endo}$, and the free water fraction ($R_f$) within the hydrogel was determined according Equation 2:

$$R_f = \frac{\Delta H_{endo}}{\Delta H_w} \qquad \text{Eq-2}$$

where $\Delta H_w$ is the heat fusion of pure water (332.2 mJ/mg) [6].

In Vitro Retention and Sustained Release of rhBMP-2

Recombinant protein rhBMP-2 (R&D Systems, CHO-derived) was reconstituted according to vendor specifications and diluted with $Ca^{2+}/Mg^{2+}$-free Dulbecco's phosphate-buffered saline (DPBS, pH 7.4) to a loading concentration of 30 ng/µL. Hydrogels retrieved from the sterile stock solution were partially dried in a sterile cell culture hood (with a gel volume reduction of 50 to 100 $mm^3$), and then transferred into the wells of ultra-low attachment 24-well plate (Corning). Reconstituted rhBMP-2 solution (10 µL, 30 ng/µL) was placed on each hydrogel to achieve a total loading dose of 300-ng rhBMP-2/hydrogel (cylindrical), and allowed to be incubated at 37° C. for 1 h (during which rhBMP-2 solutions were fully absorbed by the hydrogels). The rhBMP-2 loaded hydrogels were then incubated in 1 mL of DPBS at 37° C. for 2, 4, 6, 10, and 24 h. Concentration of the released rhBMP-2 in the DPBS at various time points were determined by an enzyme-linked immuno sorbent assay (ELISA) using a rhBMP-2 Quantikine Kit (R&D Systems) and the amount of the rhBMP-2 released form hydrogels were calculated from the standard curve generated during the same experiment. A sample size of 3 was applied to each hydrogel group.

Bioactivity of the rhBMP-2 Sequestered on & Released from the Hydrogels

The bioactivity of the rhBMP-2 retained on and subsequently released from the PEGMA and PSBMA hydrogels was evaluated by their ability to induce osteogenic trans-differentiation of murine myoblast C2C12 cells into osteoblasts. (Liu, et al. 2011 Acta Biomaterialia 7:3488-95; Filion, et al. 2011 Tissue Engineering Part A 17:503-11.) C2C12 cells were seeded on 24-well cell culture plate (10,000 cells/cm$^2$) in 1 mL of Dulbecco's modified eagle medium (DMEM) supplemented with 10% fetal bovine serum and 1% penicillin/streptomycin, and allowed to attach overnight. The medium was then replaced with fresh DMEM supplemented with 5% fetal bovine serum and 1% penicillin/streptomycin, and the rhBMP-2 loaded hydrogels retrieved from prior incubation in PBS up to 6 days were placed in the adherent C2C12 culture. After 3 days, the hydrogel was removed and the cells were fixed and stained for alkaline phosphatase (ALP) using a Sigma Leukocyte Alkaline Phosphatase Kit according to the vender's protocol. C2C12 culture directly supplemented with 300-ng rhBMP-2 without any hydrogel carrier served as a positive control.

Animal Surgical Procedures

All animal procedures were approved by the University of Massachusetts Medical School Institutional Animal Care and Use Committee. Briefly, male Charles River SASCO-SD rats (289-300 g) were sedated and maintained by 2% isoflurane-oxygen throughout the surgery. The mid-shaft of a femur was exposed by a combination of sharp and blunt dissections and the periosteum of the exposed femur was circumferentially removed to emulate a challenging clinical scenario where this important source of progenitor cells and signaling molecules is lost. (Filion, et al. 2011 Tissue Engineering Part A 17:503-11.) A radiolucent, weight bearing polyetheretherketone (PEEK) internal fixation plate was secured to the exposed femur with four bicortical screws into predrilled holes. A 5-mm mid-diaphyseal defect was then created using an oscillating Hall saw with parallel blades. The defect site was thoroughly irrigated with saline to remove bone debris and residue detached periosteum before it was press-fit with a hydrogel graft with or without 500-ng rhBMP-2 (FIG. 3a, n=4). The muscle and skin were closed with resorbable sutures and the rats were given cefazolin (20 mg/kg, once a day) and bupenorphine (0.08 mg/kg, 3 times a day) injections subcutaneously over the next 2 days. Rats were radiographed biweekly post-op to ensure proper graft positioning, and subjected to monthly longitudinal microCT (μ-CT) scans (n=4) to quantitatively monitor the mineralized callus formation until time of sacrifice at 12 weeks post-op. For end-time point analyses, the femur, with the PEEK plate fixator intact, was carefully separated from the adjacent hip and knee joints for either torsion test (n=3) or histological staining. In a second set of experiments, implants were retrieved at 2 and 7 days post-op (n=2) for examination of cellular attachment on the surface of the implant.

Longitudinal μ-CT Analysis

Rats were scanned immediately post-op and every 4 weeks thereafter on a viva-CT 75 in vivo Micro-CT system (SCANCO Medical AG) to monitor new bone formation over time. The effective voxel size of the reconstructed images was 30×30×30 μm$^3$. Data were globally thresholded and 3D images of the 5-mm defect, defined as the region of interest (ROI, 167 slices, 30 μm/slice), were reconstructed for quantification of bone volume (BV, mm$^3$) and bone mineral density (BMD, mgHA/ccm). Two-dimensional (2D) mineral density color mapping was generated by reconstructing the respective AIM file with a colored density gradient range of 1.5-3.5 (1/mm). An unimplanted PSBMA hydrogel was scanned to guide proper setting of the threshold (to eliminate hydrogel background) for all analyses.

Torsion Test

Explanted femora were torqued to failure as previously described to assess the degree of the functional restoration of their biomechanical integrity. (Filion, et al. 2011 Tissue Eng Pt A 17:503-11.) Briefly, explant was potted in stainless steel hexanuts with poly(methyl methacrylate). The PEEK plate fixators were either carefully bisected without disturbing the underlying graft/new bone using a high-speed burr (the PSBMA group) or unscrewed and removed from the explants (rhBMP-2 treated group) before mounted on the mini-torsion tester (ADMET Inc.). Each specimen was torqued to failure at 1°/s.

Histology

The explants were fixed by 10% zinc formalin for 24 h, decalcified in 18% EDTA at 4° C. for 4 weeks, and embedded with glycol methacrylate and sectioned. The 3-μm sections were mounted onto slides for hematoxylin & eosin (H&E) staining.

Early-Stage In Vivo Cell Attachment on Implant Surfaces

To visualize the in vivo cell attachment to the hydrogel scaffolds during the early stage of guided bone regeneration, the hydrogel implants with/without pre-loaded rhBMP-2 (500 ng/hydrogel) were retrieved at 2 and 7 days post-op. The explants were fixed in 3.7% formaldehyde/DPBS solution, and the adherent cells were stained with Alexa Fluoro 488 phalloidin (for F-actin staining, red) and DAPI (for nuclei staining, blue) following the vendor's protocol, respectively, and imaged on a Leica TCS SP2 confocal microscope. Phalloidin was excited at 495 nm and observed with a 518-nm filter while DAPI was excited at 368 nm and observed with a 461-nm filter.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A method for sustained release of a protein in vivo, comprising:
   placing an implant in vivo, wherein the implant consists of a crosslinked 3-dimensional zwitterionic polymer and a protein, wherein the protein is encapsulated in the crosslinked 3-dimensional zwitterionic polymer and is characterized by preserved bioactivity as sequestered; and
   causing release of the encapsulated protein from the implant at a rate such that greater than 65% of the protein remains encapsulated after 24 hours, wherein the protein is characterized by preserved bioactivity as released,
   wherein
   the crosslinked 3-dimensional zwitterionic polymer is polymethacrylate, polyacrylate, polymethacrylamide or polyacrylamide crosslinked with poly (ethylene glycol) dimethacrylate, poly(ethylene glycol) diacrylate, ethylene glycol diacrylate or ethylene glycol dimethacrylate, and
   the protein is a therapeutic osteogenic protein.

2. A method for promoting bone healing with a protein, comprising:
   placing an implant in vivo, wherein the implant consists of a crosslinked 3-dimensional zwitterionic polymer and a protein, wherein the protein is encapsulated in the crosslinked 3-dimensional zwitterionic polymer and is characterized by preserved bioactivity as sequestered; and
   causing release of the encapsulated protein from the implant, wherein the released protein is characterized by preserved bioactivity thereby promoting bone healing, wherein
   the crosslinked 3-dimensional zwitterionic polymer is polymethacrylate, polyacrylate, polymethacrylamide or polyacrylamide crosslinked with poly (ethylene glycol) dimethacrylate, poly(ethylene glycol) diacrylate, ethylene glycol diacrylate or ethylene glycol dimethacrylate, and
   the protein is a therapeutic osteogenic protein.

3. A method for treating a bone defect, comprising:
   placing an implant in vivo, wherein the implant consists of a crosslinked 3-dimensional zwitterionic polymer and a protein, wherein the protein is encapsulated in the crosslinked 3-dimensional zwitterionic polymer and is characterized by preserved bioactivity as sequestered; and
   causing release of the encapsulated protein from the implant to treat the bond defect, wherein the released protein is characterized by preserved bioactivity, wherein
   the crosslinked 3-dimensional zwitterionic polymer is polymethacrylate, polyacrylate, polymethacrylamide or polyacrylamide crosslinked with poly (ethylene glycol) dimethacrylate, poly(ethylene glycol) diacrylate, ethylene glycol diacrylate or ethylene glycol dimethacrylate, and
   the protein is a therapeutic osteogenic protein.

4. A method for performing tissue grafting or engineering, comprising:
   placing a tissue grafting or engineering scaffold in vivo, wherein the tissue grafting or engineering scaffold consists of a crosslinked 3-dimensional zwitterionic polymer and a protein, wherein the protein is encapsulated in the crosslinked 3-dimensional zwitterionic polymer and is characterized by preserved bioactivity as sequestered; and
   causing release of the encapsulated protein from the tissue grafting or engineering scaffold to facilitate tissue regeneration, wherein the released protein is characterized by preserved bioactivity, wherein
   the crosslinked 3-dimensional zwitterionic polymer is polymethacrylate, polyacrylate, polymethacrylamide or polyacrylamide crosslinked with poly (ethylene glycol) dimethacrylate, poly(ethylene glycol) diacrylate, ethylene glycol diacrylate or ethylene glycol dimethacrylate, and
   the protein is a therapeutic osteogenic protein.

5. The method of claim 1, wherein bioactivity of the encapsulated protein is preserved for at least nine days after sequestration.

6. The method of claim 1, wherein the therapeutic osteogenic protein is selected from BMPs, TGF-beta, EGF, FGF, IGF-1 and VEGF.

7. The method of claim 1, wherein the zwitterionic moiety comprises one or more selected from sulfobetaine, phosphorylcholine and carboxybetaine.

8. The method of claim 7, wherein the zwitterionic moiety is present in the polymer as pendant groups to a polymeric backbone.

9. The method of claim 8, wherein the composite material is biodegradable.

10. The method of claim 9, wherein the zwitterionic moiety is present in the polymer at a density from about 0.05 mol % to about 10 mol %.

* * * * *